United States Patent [19]
Tanaka et al.

[11] Patent Number: 4,834,051
[45] Date of Patent: May 30, 1989

[54] OXYGEN SENSOR AND AN AIR-FUEL RATIO CONTROL APPARATUS OF AN INTERNAL COMBUSTION ENGINE USING THE SAME

[75] Inventors: Masahi Tanaka, Takatsuki; Shigekazu Yamauchi, Nagaokakyo; Masaru Mikita, Kyoto, all of Japan

[73] Assignee: Mitsubishi Jidosha Kogyo Kabushiki Kaisha, Tokyo, Japan

[21] Appl. No.: 166,968

[22] Filed: Mar. 11, 1988

[30] Foreign Application Priority Data

| Mar. 13, 1987 | [JP] | Japan | 62-35985 [U] |
| Mar. 13, 1987 | [JP] | Japan | 62-35986 [U] |
| Mar. 19, 1987 | [JP] | Japan | 62-39202 [U] |
| Nov. 5, 1987 | [JP] | Japan | 62-280130 |
| Nov. 5, 1987 | [JP] | Japan | 62-280129 |
| Nov. 5, 1987 | [JP] | Japan | 62-280128 |
| Nov. 5, 1987 | [JP] | Japan | 62-280127 |

[51] Int. Cl.$^4$ .............. F02D 41/14; G01N 27/46
[52] U.S. Cl. ................ 123/440; 123/489; 204/426; 204/429
[58] Field of Search .............. 123/440, 489; 204/424, 204/425, 426, 427, 428, 429

[56] References Cited

U.S. PATENT DOCUMENTS

| 4,132,615 | 1/1979 | Linder et al. | 204/428 |
| 4,569,748 | 2/1986 | Yamakawa et al. | 204/429 |
| 4,574,042 | 3/1986 | Shiraishi | 204/429 |
| 4,584,086 | 4/1986 | Hayakawa et al. | 204/429 |
| 4,626,338 | 12/1986 | Kondo et al. | 204/429 X |
| 4,741,817 | 3/1988 | Croset et al. | 204/429 X |
| 4,773,376 | 9/1988 | Uchikawa et al. | 123/489 |

FOREIGN PATENT DOCUMENTS

| 2341256 | 2/1975 | Fed. Rep. of Germany | 204/429 |
| 2738882 | 3/1978 | Fed. Rep. of Germany | 204/429 |
| 0044689 | 4/1977 | Japan | 204/429 |
| 0012002 | 3/1982 | Japan . |
| 0054854 | 4/1982 | Japan | 204/429 |
| 0256045 | 12/1985 | Japan . |

Primary Examiner—Willis R. Wolfe
Attorney, Agent, or Firm—Frishauf, Holtz, Goodman & Woodward

[57] ABSTRACT

An oxygen sensor having a detecting element for detecting the concentration of oxygen contained in a subject gas. The subject gas reaches the detecting element through a carrier carrying a substance which adsorbs or desorbs the oxygen in the subject gas in accordance with the partial pressure of the oxygen. Thus, the detecting element is prevented from being corrupted by $O_2$ or CO. Even though the oxygen sensor is temporarily exposed to excessive $O_2$ or CO, therefore, the responsiveness of oxygen concentration detection to be effected thereafter is improved. Cerium oxide or lanthanum oxide may be suitably used as the oxygen adsorbing or desorbing material. The carrier may be pellets surrounding the oxygen detecting element, or a protective layer or a buffer layer formed on the surface of the detecting element. Alternatively, the carrier may be formed independently of the oxygen sensor so as to be disposed in an exhaust passage on the upper-course side of the oxygen sensor. The oxygen sensor of the present invention is adapted for use in an air-fuel ratio control apparatus of an internal combustion engine.

27 Claims, 10 Drawing Sheets

OXYGEN SENSOR AND AN AIR-FUEL RATIO CONTROL APPARATUS OF AN INTERNAL COMBUSTION ENGINE USING THE SAME

BACKGROUND OF THE INVENTION

The present invention relates to an oxygen sensor adapted for the air-fuel ratio control of, for example, a vehicular internal combustion engine, and an air-fuel ratio control apparatus of an internal combustion engine using the oxygen sensor.

In internal combustion engines of automobiles and the like, the air-fuel ratio of an air-fuel mixture supplied thereto should be controlled so as to be always in the vicinity of the stoichiometric (SM) ratio or the theoretical air-fuel ratio, in order to make the most of the engine performance. This air-fuel ratio control is very important also because a three-way catalyst, which is used to remove harmful substances in exhaust gas, serves to simultaneously remove, with high efficiency, CO, $NO_X$, and HC from exhaust gas which is produced when an air-fuel mixture having an air-fuel ratio controlled within a very narrow range in the vicinity of the aforesaid stoichiometric value is burned.

An air-fuel ratio control apparatus is used for the air-fuel ratio control of these internal combustion engines. The control apparatus of this type serves to control the injection quantity of a fuel injection valve in accordance with an oxygen concentration detection signal delivered from an oxygen sensor, which is disposed, for example, in an exhaust passage of the engine, on the upper-course side of the three-way catalyst.

More specifically, when the air-fuel ratio of the air-fuel mixture supplied to the engine varies between the fuel-rich and -lean sides, with respect to the stoichiometric ratio, the concentration of oxygen in the exhaust gas changes, so that the output value of the oxygen sensor also changes across predetermined discrimination value $V_X$. An electronic control unit varies the amount of fuel supply in accordance with the output value of the oxygen sensor, more specifically, the direction of the change of the sensor output value with respect to predetermined discrimination value $V_X$, and the time elapsed after value $V_X$ is crossed by the sensor output value. Thus, the air-fuel ratio is controlled in the vicinity of the stoichiometric ratio.

In a practical oxygen sensor adapted for such air-fuel ratio control, an oxygen ion conducting solid electrolyte is held between a pair of electrodes, which are brought into contact with atmospheres containing oxygen at different concentrations, thus forming an oxygen concentration cell. The concentration of oxygen in the subject gas is measured by means of the electromotive force of the concentration cell.

In this prior art oxygen sensor, the oxygen ion conducting solid electrolyte is sandwiched, for example, between the electrodes, which are formed of a porous, gas-permeable material such as platinum (Pt), and a protective layer of a porous ceramic material is formed on the surface of that one of the electrodes in contact with the subject gas.

An alternative example of the conventional oxygen sensor comprises an insulating supporter, formed of e.g. alumina, and an oxygen concentration detecting element disposed in the supporter. The detecting element is composed of a chip and a pair of Pt electrodes. The chip is disposed in a rectangular recess in one side face of the supporter so that its one side face is exposed. The Pt electrodes, which are connected to the back face of the chip, is used to detect the change of the electric resistance of the chip. The chip is formed of titanium ($TiO_2$) or some other material which changes its internal electric resistance when it is touched by oxygen, depending on the oxygen concentration.

Generally, however, the conventional oxygen sensors are low in responsiveness. The trouble, therefore, is that once the air-fuel ratio shifts considerably to the lean side due to acceleration of an automobile, for example, the oxygen sensor continues to deliver a lean signal to the electronic control device, even though the air-fuel ratio actually is returned substantially to the stoichiometric value on the rich side. Properly speaking, the air-fuel ratio of the air-fuel mixture supplied to the engine should be adjusted to a value approximate to the stoichiometric value immediately after the end of the acceleration. Due to the response delay of the oxygen sensor, however, a so-called rich excursion occurs such that the ratio deviates to the rich side by a large margin.

In contrast with this, when the air-fuel ratio of the mixture is returned to the value near the stoichiometric air-fuel ratio after it is shifted substantially to the rich side, the oxygen sensor awkwardly continues to deliver a rich signal.

Thus, if the air-fuel ratio of the air-fuel mixture supplied to the engine deviates from the stoichiometric value, the purifying capability of CO, HC, and $NO_X$ of the three-way catalyst decreases sharply, so that the concentrations of these substances in the exhaust gas increase.

These problems have been solved by the development of an improved oxygen sensor which is disclosed in Japanese Patent Disclosure No. 60-256045. In this sensor, the electrodes are formed of an electrically conductive material which is prepared by adding rhodium and at least an oxide of a rare-earth element to platinum. Thus, the catalyst activity of the electrodes is improved, and the response speed of the oxygen sensor is increased.

Disclosed in Japanese Patent Publication No. 57-12002 is an exhaust emission control device which uses an oxygen sensor located on the upper-course side of a three-way catalyst. In this device, a catalytic element having the same catalytic function as the three-way catalyst is disposed in the oxygen sensor itself or on the upper-course side thereof. According to this arrangement, the position in which the oxygen concentration detecting performance of the oxygen sensor, as compared with the air-fuel ratio, suddenly changes can be brought in line with the position in which the optimum purification efficiency of the catalyst can be obtained. Thus, the three-way catalyst can be worked effectively.

OBJECTS AND SUMMARY OF THE INVENTION

The primary object of the present invention is to provide an oxygen sensor capable of detecting the change of the concentration of oxygen contained in exhaust gas as soon as possible.

Another object of the invention is to provide an oxygen sensor which is adapted for the air-fuel ratio control of an internal combustion engine of a vehicle or the like, using a three-way catalyst disposed in an exhaust passage, and can prevent lowering of the exhaust purification efficiency of the three-way catalyst, without entailing the so-called rich excursion, despite a substantial temporary increase in the amount of oxygen in the exhaust passage, during the acceleration of the vehicle, for example.

Still another object of the invention is to provide an air-fuel ratio control apparatus of an internal internal combustion engine which is adapted for the air-fuel ratio control of a vehicular internal combustion engine or the like, and can detect the concentration of oxygen contained in exhaust gas, following up drastic changes of the air-fuel ratio due to acceleration or the like as far as possible, thereby effecting the air-fuel ratio control with higher accuracy.

The present invention is based on the understanding that the responsiveness of an oxygen sensor can be lowered if the sensor is exposed to excessive $O_2$ gas or CO gas and is corrupted thereby. Such corruption can be avoided by preventing excessive $O_2$ or CO gas from reaching an oxygen detecting element with use of substance which, located beside the detecting element, serves to adsorb or desorb oxygen in accordance with the partial oxygen pressure.

According to the present invention, there is provided an oxygen sensor which has a detecting element for detecting the concentration of oxygen contained in a subject gas. The oxygen sensor of the invention comprises a carrier carrying a substance which adsorbs or desorbs the oxygen in the subject gas in accordance with the partial pressure of the oxygen. The subject gas reaches the detecting element through the carrier. Thus, the detecting element is prevented from being corrupted by $O_2$ or CO. Even though the oxygen sensor is temporarily exposed to excessive $O_2$ or CO, therefore, the responsiveness of oxygen concentration detection to be effected thereafter is improved.

According to an aspect of the present invention, the detecting element may be composed of an oxygen ion conducting solid electrolyte layer and a pair of electrodes holding the solid electrolyte layer therebetween. Alternatively, the detecting element may include a protective layer besides the electrolyte layer and the electrodes. In this case, the protective layer is formed on the outer surface of the subject-side electrode, out of the paired electrodes.

According to another aspect of the invention, the detecting element may be composed of an insulating supporter, a chip disposed on one side face of the supporter, and a pair of electrodes spaced at a predetermined distance from each other and connected to the chip, the chip being formed of a material, preferably titanium oxide, which changes its electric resistance in accordance with the concentration of oxygen.

The carrier may be pellets filling a gap between the detecting element and the inner wall of a protector pipe which contains the detecting element and formed with a number of small holes. In an alternative arrangement, the carrier may be the protective layer of the detecting element, or a buffer layer formed on the outer surface of the subject-side electrode, out of the paired electrodes of the detecting element. Alternatively, moreover, the carrier may be a porous layer covering the subject-side surface of the chip of the detecting element. Alternatively, furthermore, the carrier may be formed independently of the oxygen sensor, and be disposed in the exhaust passage on the upper-course side of the oxygen sensor.

Cerium oxide, lanthanum oxide, etc., may be suitably used as the substance to adsorb or desorb the oxygen.

If the pellets are used as the carrier, the amount of the substance to adsorb or desorb the oxygen contained in the pellets ranges from 4 to 80 g/l, preferably from 8 to 40 g/l as calculated in terms of a metal constituting the substance. If the protective layer or the buffer layer is used as the carrier, the ratio of the absorbing or desorbing substance contained in the layer ranges form 0.8 to 16% by weight, preferably from 1.6 to 8% as calculated in terms of a metal constituting the substance.

The oxygen sensor of the present invention is adapted for use in an air-fuel ratio control apparatus of an internal combustion engine.

The above and other objects, features, and advantages of the invention will be more apparent from the ensuing detailed description taken in connection with the accompanying drawings.

DETAILED DESCRIPTION

Figure 1:
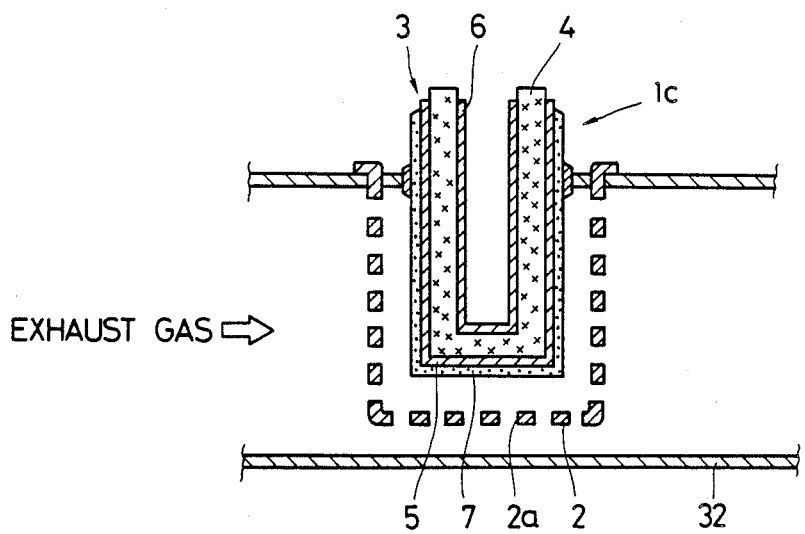
FIG. 1 is a vertical sectional view schematically showing an arrangement of a prior art oxygen sensor.

FIG. 1 shows an example of a prior art oxygen sensor used for the air-fuel ratio control of an internal combustion engine. The oxygen sensor 1C comprises a protector pipe 2 fixedly inserted in an exhaust passage 32, which is connected to the engine, and an oxygen detecting element 3 contained in the pipe 3. The protector pipe 2 has a number of small holes 2a throughout its wall surface, through which a subject gas, i.e., exhaust gas, is passed. The oxygen detecting element 3 includes, for example, an oxygen ion conducting solid electrolyte 4, electrodes 5 and 6 disposed on either side of the electrolyte 4, and a protective layer 7 formed on the surface of the electrode 5 which is touched by the subject gas. Generally, stabilized zirconia is used for the solid electrolyte 4, while gas-permeable porous platinum (Pt) or the like is used for the electrodes 5 and 6. Spinel or other porous ceramic material is used for the protective layer 7.

Figure 2:
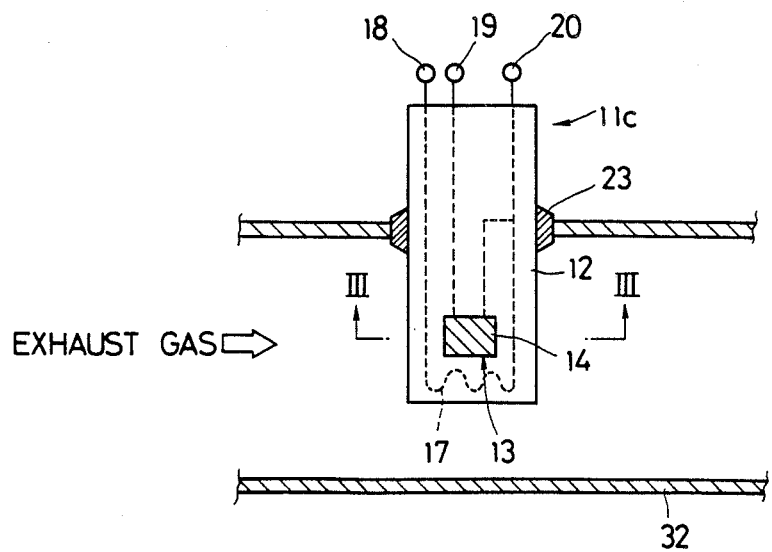
FIG. 2 is a vertical sectional view schematically showing an arrangement of another prior art oxygen sensor.
Figure 3:
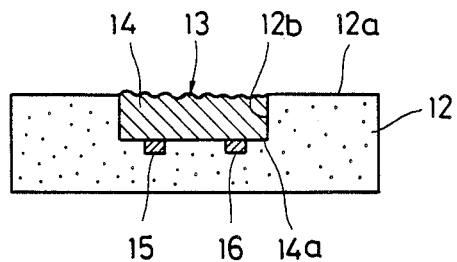
FIG. 3 is a sectional veiw taken along line III—III of FIG. 2.

FIGS. 2 and 3 show an arrangement of another prior art oxygen sensor. An oxygen sensor 11C comprises an insulating supporter 12, formed of e.g. alumina, and an oxygen concentration detecting element 13 contained in the supporter 12. The oxygen concentration detecting element 13 is composed of a chip 14 and a pair of Pt electrodes 15 and 16. The chip 14 is disposed in a rectangular recess 12b in one side face 12a of supporter 12 so that its one side face is exposed. The electrodes 15 and 16, which are connected to a back face 14a of the chip 14, is used to detect the change of the internal electric resistance of the chip. The chip 14 is formed of titanium oxide ($TiO_2$; hereinafter referred to as titania) or some other material which changes its internal electric resistance when it is touched by oxygen, depending on the oxygen concentration.

The electrodes 15 and 16 are connected to an output terminal 19 and an earth terminal 20, respectively. Since titania changes its internal resistance according to temperature, it must be kept at a predetermined temperature lest the detected value of oxygen concentration be influenced by ambient temperature. To this end, a heater 17 is located close to the chip 14, whereby the chip is kept at the predetermined temperature, more specifically, a temperature higher than the exhaust gas temperature. The heater 17 is connected to a power supply terminal 18 and the earth terminal 20. Constructed in this manner, the oxygen sensor 11C is mounted inside the exhaust passage 32 of the engine with the aid of a sealing member 23, for example.

Figure 4:
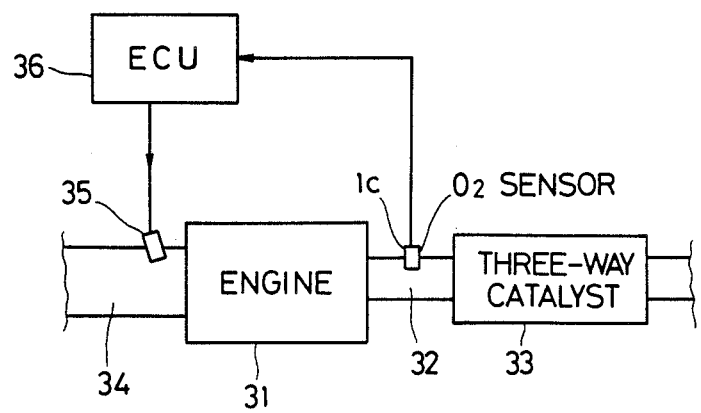
FIG. 4 is a block diagram schematically showing an arrangement of an air-fuel ratio control apparatus of a prior art internal combustion engine.

These prior art oxygen sensors are used in an air-fuel ratio control apparatus of the construction shown in FIG. 4. The air-fuel ratio control apparatus comprises, for example, the oxygen sensor 1C of the type shown in FIG. 1, fuel injection valves 35, and an electronic control unit (ECU) 36. The sensor 1C is located on the upper-course side of the exhaust passage 32 of an internal combustion engine 31, with respect to a three-way catalyst 33, while the injection valves 35 are disposed in a suction passage 34. The electronic control unit 36, which is connected electrically with the oxygen sensor 1C, serves to control the injection quantity of the fuel injection valves 35 in accordance with an oxygen concentration detection signal delivered from the sensor 1C. A throttle opening sensor, crank angle position sensor, engine water temperature sensor, and other sensors (not shown) for detecting various engine operation parameter are connected electrically to the input side of the electronic control unit 36.

Figure 5:
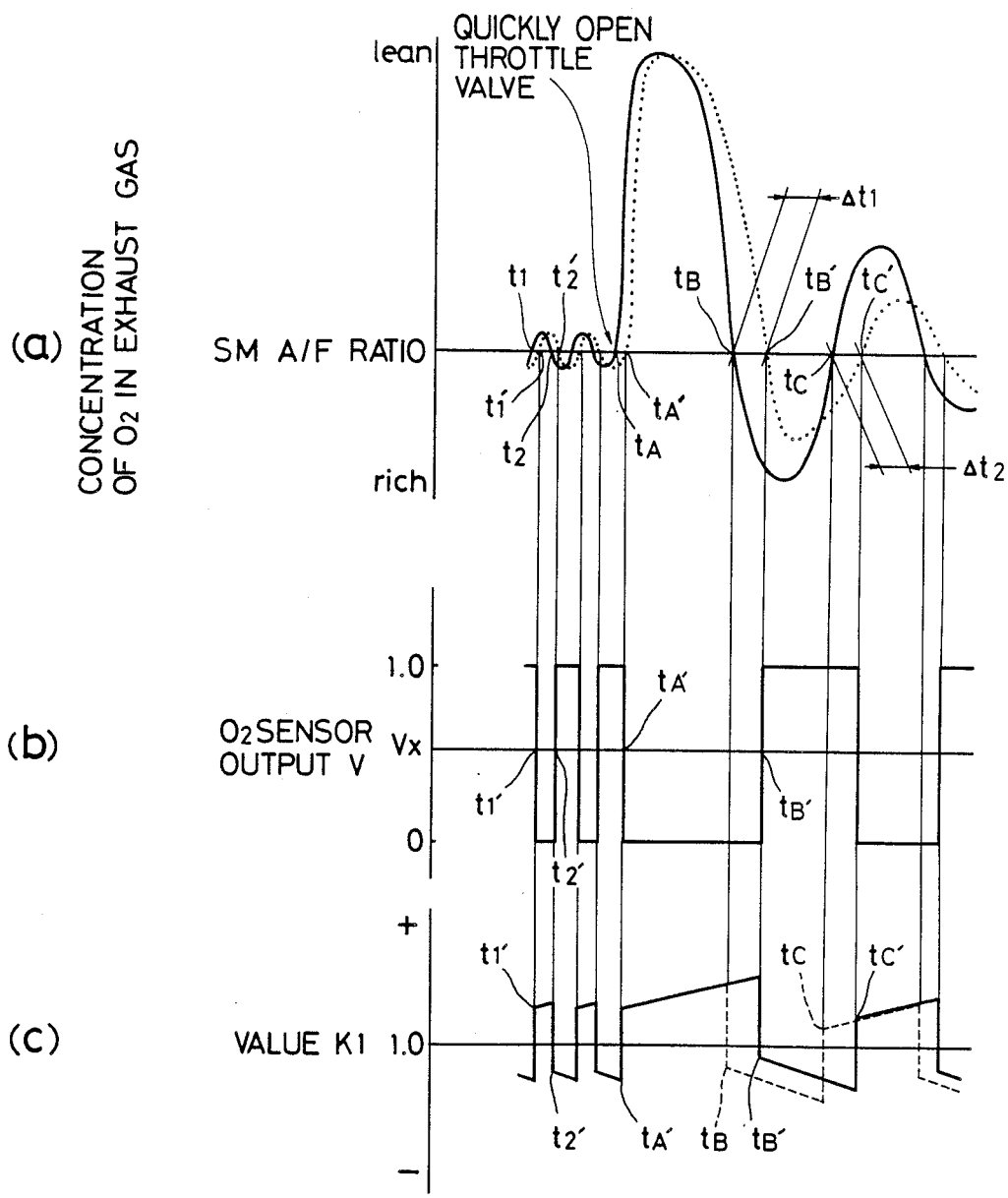
FIGS. 5(a), 5(b) and 5(c) are timing charts for illustrating the relationships between time-based transitions of the concentrations of oxygen in the vicinity of the prior art oxygen sensor for air-fuel ratio control, disposed in an exhaust passage, and of an electrode portion of the sensor, the value of an oxygen concentration detection signal delivered from the sensor, and the value of feedback correction factor K1 used to correct the injection quantity of a fuel injection valve, the relationships corresponding to the air-fuel ratio of an air-fuel mixture supplied to the engine.

Referring now to FIGS. 5(a), 5(b) and 5(c), operation for the air-fuel ratio control by means of the air-fuel ratio control apparatus, using one such prior art oxygen sensor, will be described. In FIG. 5(a), a full-line curve indicates the time-based transition of the concentration of oxygen contained in exhaust gas discharged into the exhaust passage 32, compared with the change of the air-fuel ratio of an air-fuel mixture supplied to the engine 31. In this graph, the time-based transition of the oxygen concentration is represented in terms of air-fuel ratio in place of oxygen percentage, for convenience.

Here let it be supposed that the air-fuel ratio (A/F) changes so that the oxygen concentration in the exhaust passage 32 changes from the fuel-rich side to the fuel-lean side at time t1. The oxygen sensor 1C detects this change of the air-fuel ratio at time t1', and its output value drops across predetermined discrimination value $V_x$, as shown in FIG. 5(b). When the air-fuel ratio further changes from the fuel-lean side to the fuel-rich side at time t2, the output value of the oxygen sensor 1C rises again across discrimination value $V_x$ at time t2'. At this time, the electronic control unit 36 varies the amount of fuel supply in accordance with the output value of the oxygen sensor 1C, more specifically, the direction of the change of the sensor output value with respect to discrimination value $V_X$, and the time elapsed after the change across value $V_X$. Thus, the control unit 36 executes fuel supply control based on a feedback control mode. In this feedback control mode, fuel injection period T of the fuel injection valve 35 is calculated as follows:

$$T = T_B \times K1 \times K2 \times C + T_D$$

where $T_B$ is a basic injection period; K1, a correction factor composed of a feedback proportional term and an integral term, which depends on voltage value V detected by means of the oxygen sensor; K2, a correction factor determined by the engine water temperature, throttle opening, atmospheric pressure, etc.; $T_D$, a correction factor determined in accordance with battery voltage and the like; and C, a constant. FIG. 5(c) shows the change of correction factor value K1. The proportional term value of value K1 is set to a value smaller by a predetermined margin, which changes the air-fuel ratio of the exhaust gas to the rich side, if it is concluded that the ratio is changed from rich to lean. If it is concluded that the ratio is changed from lean to rich, on the other hand, the proportional term value is set to a value greater by a predetermined margin, which changes the air-fuel ratio to the lean side. The integral term value is set to a value reduced or increased by a predetermined fine value at a time, for example, in accordance with the change of the proportional term value for each predetermined period (e.g., each predetermined time or rotation).

Subsequently, when a throttle valve (not shown) of the engine 31 is quickly opened for acceleration at time $t_A$, for example, the concentration of oxygen in the exhaust gas increases temporarily by a large margin. After this temporary increase, if the actual oxygen concentration changes to the lean side by a margin exceeding the value corresponding to the stoichiometric (SM) air-fuel ratio at time $t_B$, the prior art oxygen sensor 1C still continues to deliver a signal to increase the fuel amount up to, for example, time $t_B'$, due to its response delay and the like. Accordingly, value K1 continues further to increase during period $\Delta t1$, from time $t_B$, at which the output of the oxygen sensor 1C is to be inverted, to time $t_B'$, as shown in FIG. 5(c). As a result, fuel injection period T of the fuel injection valve 7, given by eq. (1), increases. Thus, a so-called rich excursion occurs such that an excessive amount of fuel is supplied to the engine 31, thereby greatly deviating the air-fuel ratio to the rich side. If such a rich excursion takes place, the exhaust purifying efficiency of the three-way catalyst 33 lowers in the meantime. In consequence, a so-called rich spike occurs such that CO and HC are subject to a spike.

The aforementioned response delay of the prior art oxygen sensor 1C occurs because the platinum electrodes of the sensor 1C is temporarily exposed to excessive oxygen atmosphere to be corrupted thereby, as will be described in detail later. The same phenomenon is caused if excessive fuel is supplied to the engine 1 so that the air-fuel ratio temporarily goes to the fuel-rich side. In this case, the platinum electrodes are exposed to excessive CO to be corrupted thereby, so that the oxygen sensor 1C suffers a response delay.

Figure 6:
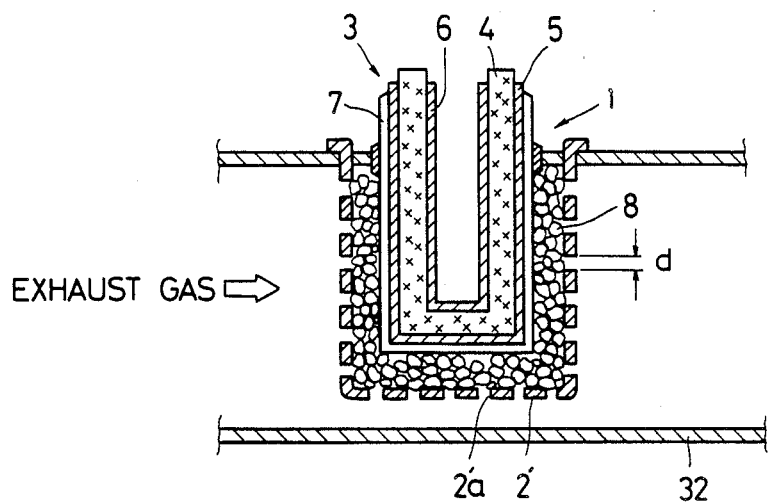
FIG. 6 is a vertical sectional view schematically showing an arrangement of an oxygen sensor according to an embodiment of the present invention, exemplifying a type such that an oxygen detecting element is surrounded by pellets carrying an oxygen storage component.

Referring now to FIG. 6, an oxygen sensor 1 according to one embodiment of the present will be described. In FIG. 6, like reference numerals refer to the same components as used in the prior art oxygen sensor 1C shown in FIG. 1.

In the oxygen sensor 1 of this embodiment, an oxygen concentration detecting element 3 is contained in a protector pipe 2'. The detecting element 3 is constructed so that an oxygen ion conducting solid electrolyte 4 is held between a first electrode 5 in contact with a subject gas, e.g., exhaust gas, and a second electrode 6 in contact with standard air, e.g., the atmosphere, the surface of the electrode 5 being coated with a protective layer 7. Although yttria-stabilized zirconia (YSZ) is preferably used for the solid electrolyte 4, calcia-stabilized zirconia (zirconia stabilized by calcium oxide) may be used instead. Platinum (Pt) is used for the electrodes 5 and 6. The protective layer 7 is formed of a porous material, such as spinel, $\gamma$-alumina, etc.

Pellets 8 fill the space between the protector pipe 2' and the outermost layer or protective layer 7 of the oxygen concentration detecting element 3. The pellets 8 carry a substance which adsorbs or desorbs oxygen in accordance with partial oxygen pressure. This substance is not limited to any specific material, and may, for example, be cerium oxide ($CeO_2$), copper oxide (CuO), or nickel oxide (NiO), which is generally known as an oxygen storage component (OSC), or lanthanum oxide ($La_2O_3$). Among these materials, cerium oxide is best suited for the purpose. The substance (hereinafter referred generally to as the oxygen storage component) to adsorb or desorb oxygen is carried by a carrier formed of alumina or the like, thus forming the pellets 8. Since alumina itself tends to adsorb or desorb oxygen without the aid of the oxygen storage component, alumina particles alone may be used for this purpose. In this case, air-permeable, porous $\gamma$-alumina is suitably used for the alumina particles. Smaller particles are preferred in order to ensure a wider surface area for adsorption. The particle diameter of the pellets 8 must be greater than the diameter d of small holes $2a'$ of the protector pipe 2'. If the particle size of the pellets 8 is too large, gaps produced when the protector pipe 2' is filled with the pellets 8 become wider, so that the exhaust gas passes without fully touching the surface of the pellets 8. It is difficult, therefore, to cause the oxygen storage component to fulfill its function. If the particle size of the pellets 8 is too small, on the other hand, the small holes $2a'$ of the protector pipe 2' must be made very small, thus entailing increase in manufacturing cost. The particle diameter of the pellets 8, which is determined in consideration of these circumstances, preferably ranges from 0.5 to 2.0 mm.

The oxygen storage component carried by the pellets 8 is not particularly limited in quantity. In the case of $CeO_2$, for example, its amount usually ranges from 4 to 80 g/l as calculated in terms of metal Ce, preferably from 8 to 40 g/l. In the cases of CuO and $La_2C_3$, the suitable amount ranges from 4 to 20 g/l as calculated in terms of metal Cu, and from 8 to 40 g/l as calculated in terms of metal La, respectively.

Throughout the description herein, the amount of the oxygen storage component carried by the carrier is given as a value calculated in terms of a metal constituting the component.

The effect of oxygen adsorption cannot be obtained if the lower limit values of these ranges are not attained. If the upper limit values are exceeded, on the other hand, the amount of adsorption is so large that the responsiveness of the oxygen sensor gets all the worse.

The pellets 8 carrying cerium oxide are formed by impregnating an alumina carrier, for example, with a predetermined amount of a cerium nitrate solution, and then sintering the resulting particles at a temperature of 500° C. or more.

Figure 7:
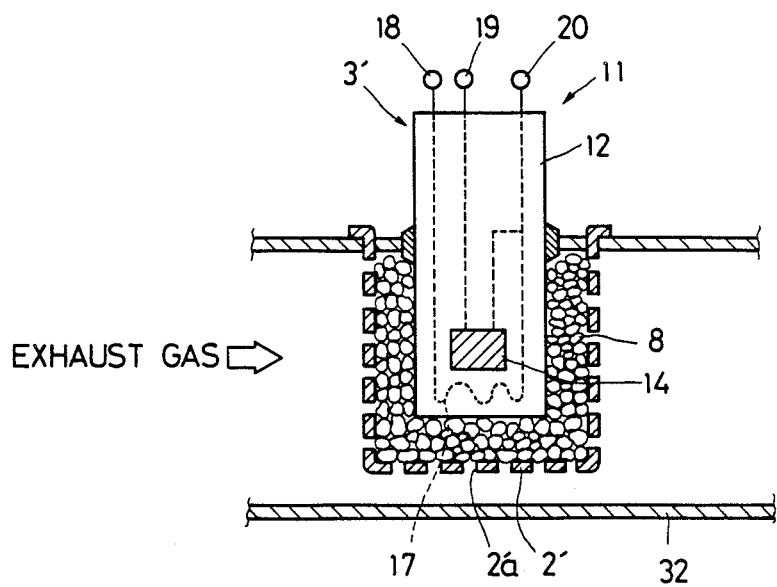
FIG. 7 is a vertical sectional view schematically showing an arrangement of an oxygen sensor according to another embodiment of the present invention of the same pellet type as the sensor shown in FIG. 6.

FIG. 7 shows an oxygen sensor 11 according to another embodiment of the present invention. The oxygen sensor 11 of this embodiment has the same construction as the one oxygen sensor 1 according to the first embodiment shown in FIG. 6, provided that titania ($TiO_2$) is used for an oxygen detecting element 3'. In FIG. 7, like reference numerals refer to the same components as used in the prior art oxygen sensor 1C shown in FIG. 2. A detailed description of these components is omitted herein.

The oxygen detecting element 3' of the oxygen sensor 11 shown in FIG. 7, like that of the prior art oxygen sensor 11C shown in FIG. 2, is composed of a chip 14 formed of titania and two Pt electrodes (not shown) fixed to the chip 14. The chip 14 is embedded in a supporter 12, formed of alumina or the like, so as to be exposed on one side face of the supporter 12. As in the case of the first embodiment shown in FIG. 6, the space between the oxygen detecting element 3' and a protector pipe 2' is filled with pellets 8 which carry an oxygen storage component, e.g., $CeO_2$.

In these oxygen sensors according to the present invention, a so-called linear sensor can be also used as the oxygen concentration detecting element.

Figure 8:
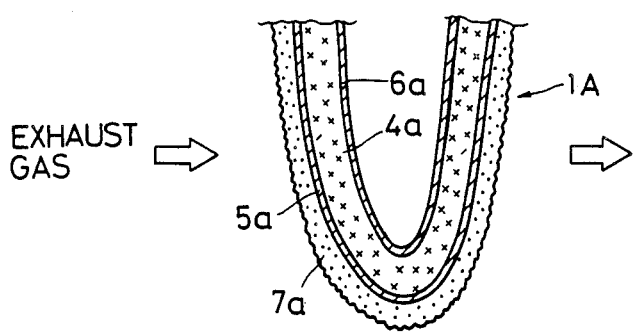
FIG. 8 is a vertical sectional view schematically showing an arrangement of an oxygen sensor according to still another embodiment of the present invention, exemplifying a type such that the oxygen storage component is carried by a protective layer.

FIG. 8 shows an oxygen sensor 1A according to still another embodiment of the present invention. In this sensor 1A, an oxygen storage component is carried by a protective layer. More specifically, an oxygen ion conducting solid electrolyte layer 4a formed of yttria-stabilized zirconia (YSZ), in the oxygen sensor 1A, is interposed between a platinum electrode 5a in contact with a subject gas, e.g., exhaust gas, and a platinum electrode 6a in contact with standard air, e.g., the atmosphere. A protective layer 7a is formed on the outer surface of the exhaust-side electrode 5a. The protective layer 7a is obtained by impregnating a porous material, such as spinel, alumina, etc., with an oxygen storage component. The oxygen storage component may, for example, be cerium oxide ($CeO_2$), lanthanum oxide ($La_2O_3$), or copper oxide (CuO), as mentioned before. Among these materials, cerium oxide is best suited for the purpose. The ratio of the oxygen storage component contained in the porous material preferably ranges from about 0.8 to 16% by weight, more preferably from 1.6 to 8% by weight as calculated in terms of a metal constituting the component. If this content ratio is lower than 0.8% by weight, hardly any effect of addition can be noticed. If the ratio exceeds 16% by weight, on the other hand, the durability of the whole protective layer lowers, and the responsiveness of the oxygen sensor gets all the worse, as mentioned later. The protective layer composed of alumina containing cerium oxide is formed, for example, by first mixing an alumina sol with cerium nitrate or cerium chloride in a predetermined ratio by weight, applying the mixture to the outer surface of the electrode 5a, drying the mixture, and then sintering the resulting structure at a temperature of 500° C. or more.

Figure 9:
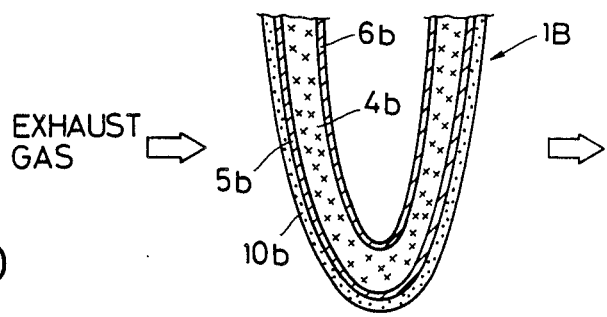
FIG. 9 is a vertical sectional view schematically showing an arrangement of an oxygen sensor according to a further embodiment of the present invention, exemplifying a type such that the oxygen storage component is carried by a buffer layer.

The carrier to carry the oxygen storage component is not limited to the protective layer, and may alternatively be a buffer layer. More specifically, FIG. 9 shows an oxygen sensor 1B according to a further embodiment of the present invention, in which an oxygen ion conducting solid electrolyte layer 4b is interposed between an electrode 5b in contact with a subject gas and an electrode 6b in contact with the atmosphere. A buffer layer 10b containing an oxygen storage component is formed on the outer surface of the subject-side electrode 5b. Yttria-stabilized zirconia is used for the electrolyte layer 4b, while platinum is used for the electrodes 5b and 6b. The oxygen storage component contained in the buffer layer 10b is not limited to any specific material, and may, for example, be cerium oxide ($CeO_2$), lanthanum oxide ($La_2O_3$), or copper oxide (CuO). Among these materials, cerium oxide is best suited for the purpose. The buffer layer 10b is formed by directly coating the outer surface of the electrode 5b with a material containing the oxygen storage component. More specifically, a heat-resistant inorganic oxide, such as spinel, silica, or alumina, is made to contain the oxygen storage component. Preferably, the ratio of the oxygen storage component contained in the inorganic oxide ranges from about 0.8 to 16% by weight.

If alumina is used as the inorganic oxide, the buffer layer 10b is formed by first mixing an alumina sol with cerium nitrate or cerium chloride in a predetermined ratio by weight, applying the mixture to the outer surface of the electrode 5b, drying the mixture, and then sintering the resulting structure at a temperature of 500° C. or more. In this arrangement, the outer surface of the buffer layer 10b may be further coated with a protective layer of spinel or alumina which serves as an oxygen diffusion layer.

Figure 10:
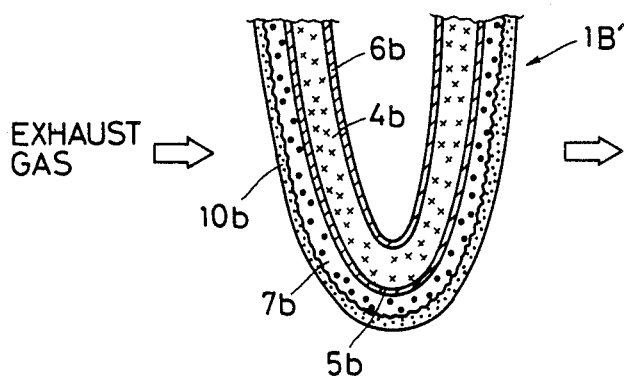
FIG. 10 is a vertical sectional view schematically showing an arrangement of an oxygen sensor according to an additional embodiment of the present invention, exemplifying a type such that a protective layer is interposed between an electrode and a buffer layer carrying the oxygen storage component.

FIG. 10 shows a modification of the oxygen sensor 1B of FIG. 9, in which a protective layer 7b is interposed between the electrode 5b and the buffer layer 10b. In FIG. 10, like reference numerals refer to the same components as shown in FIG. 9. In an oxygen sensor 1B' of this modification, the protective layer 7b serves as a diffusion layer for oxygen, and is usually formed of spinel, alumina, etc. Thus, the buffer layer 10b is formed on the outer surface of the protective layer 7b. The buffer layer 10b can be formed in the same manner as aforesaid.

Figure 11:
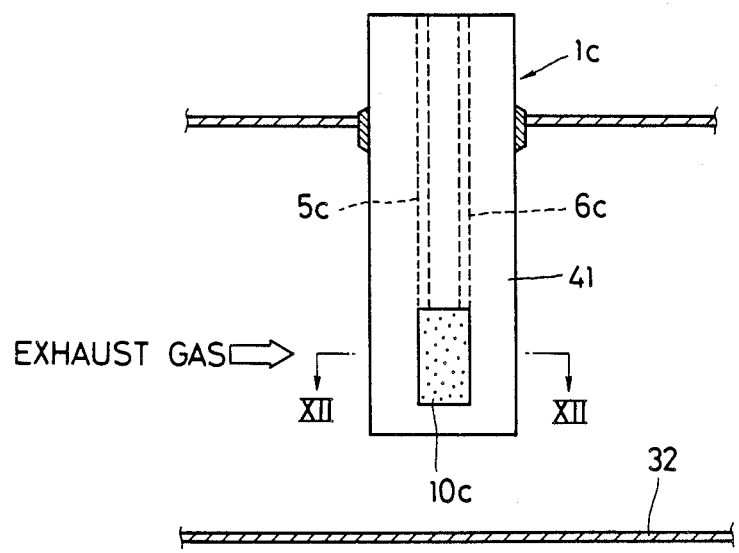
FIG. 11 is a vertical sectional view schematically showing an arrangement of an oxygen sensor according to another embodiment of the present invention, exemplifying a type such that the oxygen storage component is carried by a buffer layer.
Figure 12:
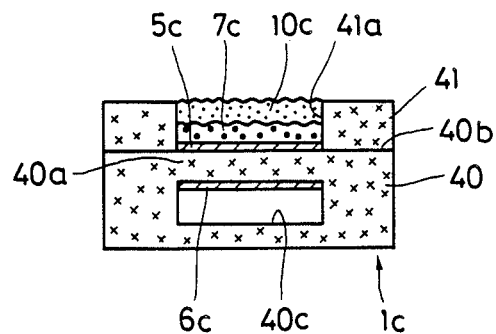
FIG. 12 is a sectional view taken along line XII—XII of FIG. 11.

FIGS. 11 and 12 show a further embodiment in which the present invention is applied to an oxygen sensor 1D of the so-called thick-film type. FIG. 11 shows a state such that the thick-film sensor 1D is disposed in an exhaust passage 32. As shown in FIG. 11, the sensor 1D comprises a supporter 40 formed of stabilized zirconia and doubling as an oxygen ion conducting solid electrolyte layer 40a, a porous layer 41 of zirconia or the like formed on one side face 40b of the supporter 40, an electrode 5c disposed in a recess 41a in the porous layer 41, a protective layer 7c, a buffer layer 10c containing an oxygen storage component, and an electrode 6c disposed in a hollow portion 40c of the supporter 40. The electrolyte layer 40a is held between the paired electrodes 5c and 6c, which are connected to their corresponding terminals (not shown). The hollow portion 40c opens to standard gas, e.g., the atmosphere.

In the thick-film sensor 1D constructed in this manner, the protective layer 7c and the buffer layer 10c can be formed in the same manner as those of the oxygen sensors 1B and 1B' shown in FIGS. 9 and 10, respectively. Since these layers 7c and 10c are embedded in the recess 41a of the porous layer 41 moreover, the resulting structure has a high mechanical strength. If a mixture of zirconia and alumina is used for the porous layer 41, furthermore, the porosity of the layer increases, and the adhesion between the layer 41 and an alumina layer, which carries an oxygen storage component, thus constituting the buffer layer 10c, is improved. In this embodiment, both the protective layer 7c and the buffer layer 10c are embedded in the recess 41a of the porous layer 41. Alternatively, however, the electrode 5c, the protective layer 7c, and the buffer layer 10c may, for example, be formed directly on the surface of the solid electrolyte layer 40a, in the order named, without using the porous layer 41.

Figure 13:
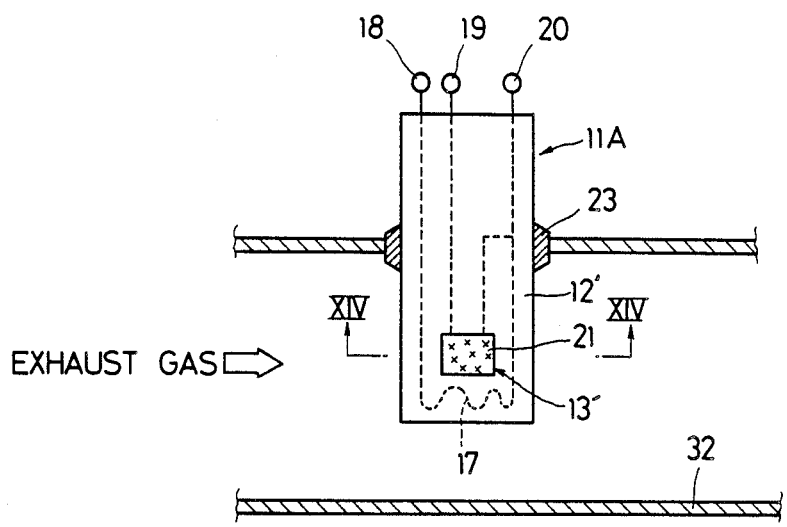
FIG. 13 is a vertical sectional view schematically showing an arrangement of an oxygen sensor according to still another embodiment of the present invention, exemplifying a type such that the oxygen storage component is carried by a porous layer.
Figure 14:
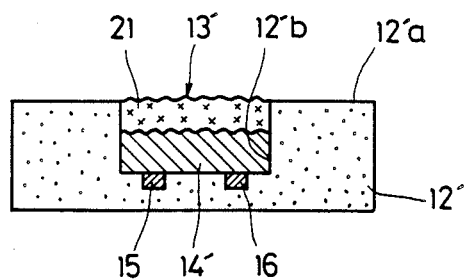
FIG. 14 is a sectional view taken along line XIV—XIV of FIG. 13.

An oxygen sensor 11A shown in FIGS. 13 and 14 is a titania sensor similar to the oxygen sensor 11 shown in FIG. 7. In this sensor 11A, a protective layer carries an oxygen storage component. In FIGS. 13 and 14, like reference numerals refer to the same components as shown in FIG. 7.

In this sensor 11A, a chip 14', rectangular in shape, for example, and a porous layer 21 are arranged successively in a recess 12b', which is formed at the lower portion of an insulating supporter 12' made of alumina or the like. The chip 14', which is adapted to touch oxygen, is formed of a material whose internal resistance varies depending on the concentration of oxygen in contact therewith. The porous layer 21 is used to carry the oxygen storage component. The chip 14', the porous layer 21, and the electrodes 15 and 16 constitute an oxygen concentration detecting element 13'. The aforementioned titania is used as the material whose internal resistance is influenced by the oxygen concentration. As the titania chip 14' and the porous layer 21 are arranged in the recess 12b' of the supporter 12' so that the outer surface of the layer 21 is flush with one side face 12a' of the supporter 12', the resulting structure can enjoy a high mechanical strength. Also, the porous layer 21 can be prevented from being separated. If the insulating supporter 12' is formed from a porous material such as alumina, moreover, the porous layer 21 is supported more firmly by an anchor effect between the layer 21 and the supporter 12'.

The oxygen storage component carried by the porous layer 21 may be cerium oxide ($CeO_2$), lanthanum oxide ($La_2O_3$), or other material mentioned before. Among these materials, cerium oxide is best suited for the purpose. The amount of the oxygen storage component carried by the layer 21 is not limited particularly. In the case of $CeO_2$, for example, the ratio of the component is usually set to 0.8 to 16% by weight, as calculated in terms of metal Ce. The porous layer 21 is formed, for example, by coating the surface of the chip 14' with a mixture of an alumina sol and cerium nitrate or cerium chloride in a predetermined ratio by weight, and then sintering the resulting structure at a temperature of 500° C. or more.

The oxygen sensor of the present invention is not limited to the aforementioned arrangement in which both the chip and the porous layer are embedded in the recess in the insulating supporter. Alternatively, only the chip may be embedded in the recess of the insulating supporter, or the chip and the porous layer may be adhered to one side face of the supporter without forming the recess in the supporter.

Figure 15:
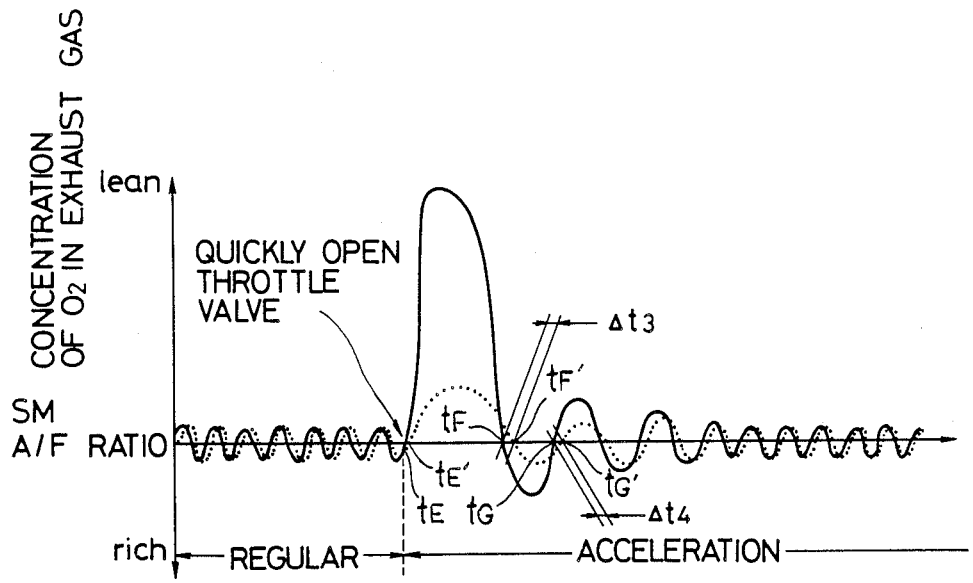
FIG. 15 is a timing chart for illustrating the relationships between time-based transitions of the concentrations of oxygen in the vicinity of the oxygen sensor for air-fuel ratio control according to the present invention, disposed in an exhaust passage, and of an electrode portion of the sensor, the relationships corresponding to the air-fuel ratio of an air-fuel mixture supplied to the engine.

The oxygen sensors according to the aforementioned various embodiments of the present invention may be suitably used in a vehicular air-fuel ratio control apparatus. Referring now to FIG. 15, the operation of these oxygen sensors, used in place of the prior art oxygen sensor 1C of the air-fuel ratio control apparatus shown in FIG. 4, will be described.

FIG. 15 is a graph similar to FIG. 5(a), showing time-based transitions of the concentration of oxygen contained in the exhaust gas discharged into the exhaust passage 32 and in the vicinity of the oxygen sensor. If the throttle valve (not shown) of an engine 31 is quickly opened to rapidly accelerate the engine 31 at time $t_E$, the oxygen storage concentration inside the exhaust passage 32 changes considerably to the lean side, as indicated by full line in FIG. 15. At this time, the oxygen storage component of the oxygen sensor of the present invention adsorbs oxygen in accordance with the partial oxygen pressure of the exhaust gas. Accordingly, the oxygen concentration in the vicinity of the electrode portion of the sensor changes as indicated by broken line in FIG. 15. Thus, the region near the electrodes cannot be exposed to excessive oxygen, so that the electrodes are prevented from being corrupted by oxygen.

The oxygen corruption of the electrodes will now be described. In the vicinity of the electrodes of the oxygen sensor, more specifically, at a so-called triple point or a three-phase interface between a solid electrolyte layer (e.g., yttria-stabilized zirconia layer), an electrode layer (e.g., platinum electrode layer), and a gas layer, gas constituents, such as $O_2$ and CO, coming close to the point are adsorbed. These adsorbed gas constituents, which are in an active state, positively react to those ones adsorbed nearby. Absorbed oxygen molecules, for example, readily react to CO molecules adjacent thereto, thus forming $CO_2$. The resulting $CO_2$ is desorbed. At this time, the velocity of reaction between the adsorbed oxygen and CO is much higher than the reaction velocity of oxygen and unadsorbed CO.

If the electrodes are corrupted by oxygen, then the adsorbable spots of the triple point are substantially occupied by oxygen gas, so that there is no room for CO or other gas ingredients to be adsorbed. In the prior art oxygen sensors, which are not provided with any carrier for carrying the oxygen storage component, the region near the electrodes is liable to be temporarily exposed to excessive oxygen. Once exposed to excessive oxygen, the triple point is occupied by the adsorbed oxygen. If CO gas reaches the point thereafter, it takes it much time to replace the oxygen. In order to be replaced by CO, oxygen must first be desorbed in linkage with unadsorbed CO, and this reaction takes much time, as mentioned before. According to the conventional oxygen sensors, therefore, once oxygen corruption occurs, it requires a lot of time thereafter to restore the state for accurate detection of the oxygen concentration. Thus, the responsiveness of these sensors cannot be high enough.

According to the oxygen sensors of the present invention, on the other hand, the oxygen storage component serves to adsorb or desorb oxygen in accordance with the partial oxygen pressure of the exhaust gas when the oxygen sensor is temporarily exposed to excessive oxygen. Accordingly, the excessive oxygen cannot reach the electrodes, so that the electrodes can be prevented from being corrupted by oxygen. If no oxygen corruption takes place, the triple point can enjoy room for the adsorption of CO, even though the concentration of oxygen in the exhaust passage temporarily becomes too high. Thus, when the concentration of oxygen contained in the exhaust gas is restored to the rich side, CO is quickly adsorbed by the remaining room therefor. The adsorbed CO reacts to the adsorbed oxygen adjacent thereto, and the resulting $CO_2$ is desorbed, so that new spaces for subsequent CO molecules are secured. Thus, oxygen is quickly replaced by CO at the triple point, and the change of the oxygen concentration of the exhaust gas is detected at high speed.

Returning now to FIG. 15, the following result will be easily inferred from the above description. If the oxygen concentration of the exhaust gas after acceleration changes to the rich side beyond the value of the stoichiometric air-fuel ratio, the change is detected after a short time delay, that is, after time period $\Delta t_3$. As a result, the air-fuel ratio of the air-fuel mixture supplied to the engine 31 can be more accurately controlled in the vicinity of the stoichiometric value, thus lowering the possibility of the so-called rich spikes.

According to the present invention, moreover, the sensor can be also effectively prevented from being corrupted by CO, in the same manner as aforesaid, when the air-fuel ratio temporarily changes to the fuel-rich side by a large margin. If the electrodes of the sensor are exposed to excessive CO, thereby suffering CO corruption, and are occupied once by adsorbed CO, oxygen, reaching the electrode portion thereafter, cannot be easily adsorbed. According to the invention, however, the oxygen sensor temporarily desorbs the adsorbed oxygen from the oxygen storage component, thereby effectively preventing the electrodes from being exposed to excessive CO, when the concentration of CO in the exhaust gas becomes too high. Thus, when the oxygen concentration inside the exhaust passage changes from the rich side to the lean side at time $t_G$, as shown in FIG. 15, the concentration change can be detected after a short time delay, that is, at time $t_G$, after time period $\Delta t_4$.

The oxygen storage component used in the oxygen sensors of the present invention hardly adsorbs or desorbs oxygen when the oxygen concentration of the exhaust gas is in the vicinity of the value corresponding to the stoichiometric air-fuel ratio. Thus, if the amount of the oxygen storage component carried by the carrier is proper, the regular air-fuel ratio control cannot be influenced by the component.

Figure 16:
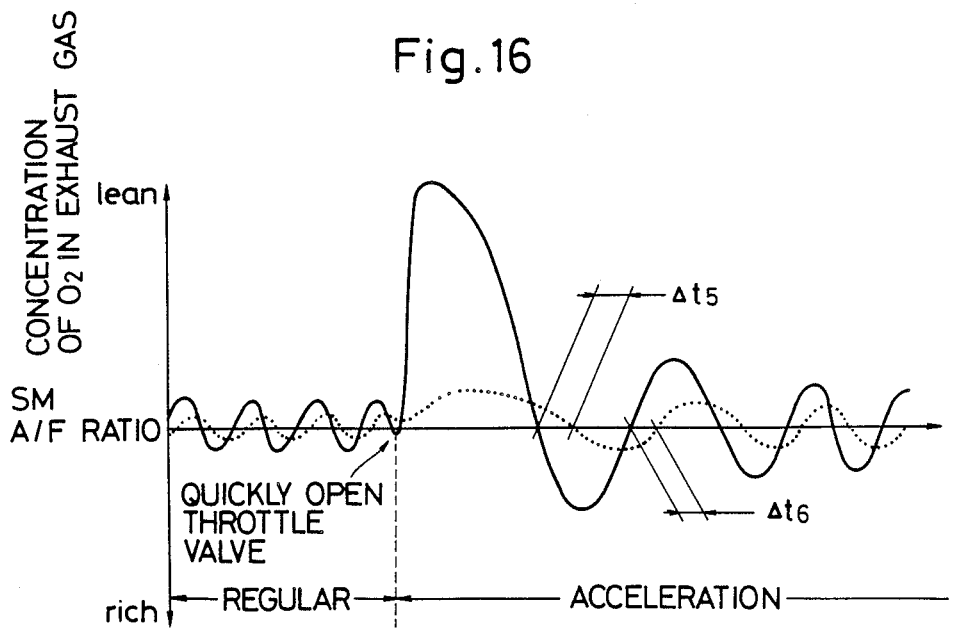
FIG. 16 is a timing chart, similar to FIG. 15, for illustrating the relationships between time-based transitions of the concentrations of oxygen obtained when air-fuel ratio control is effected by using an oxygen sensor having a carrier which carries an excessive amount of oxygen storage component.

However, if the amount of the oxygen storage component carried by the protective layer, the buffer layer, or the pellets of the oxygen sensor is too large, the responsiveness of the oxygen sensor is lowered. FIG. 16 shows transitions of the concentrations of oxygen in the vicinity of the electrodes of the oxygen sensor caused when the carried storage component is too much. In this oxygen sensor, although the electrodes are not corrupted by oxygen or CO, the time-based transition of the oxygen concentration in the vicinity of the electrodes is subject to a delay. More specifically, the time intervals $\Delta t_5$ and $\Delta t_6$ shown in FIG. 16 are longer than the corresponding time intervals shown in FIG. 15. Even in a regular operation as well as during acceleration, moreover, the responsiveness of the sensor is lowered, and the feedback period and amplitude for the air-fuel ratio control are extended. Thus, the purification efficiency of the three-way catalyst is lowered.

Figure 17:
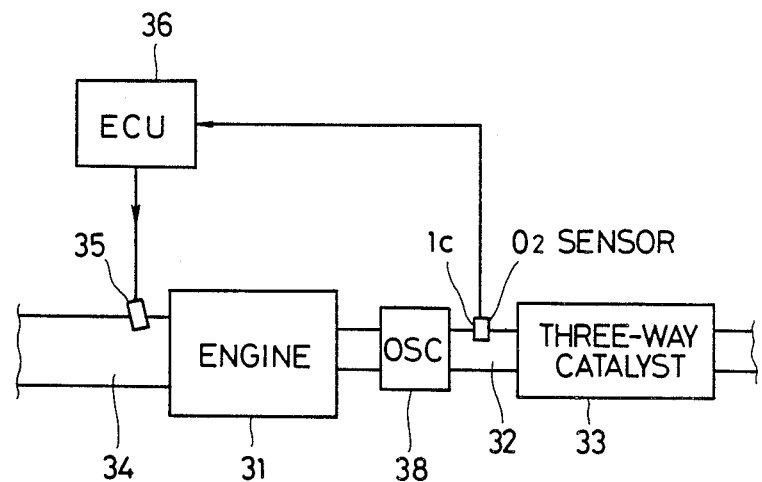
FIG. 17 is a block diagram schematically showing an arrangement of an air-fuel ratio control apparatus of an internal combustion engine according to the present invention.

As mentioned before, the oxygen storage component according to the present invention need not always be carried by any of the protective layer, the buffer layer, and the pellets in the protector pipe, of the oxygen sensor. Alternatively, as shown in FIG. 17, the same effect may be obtained by independently arranging a monolith 38, which carries the oxygen storage component, on the upper-course side of the oxygen sensor. In FIG. 17, which shows an air-fuel ratio control apparatus of an internal combustion engine according to the present invention, like reference numerals are used to designate substantially the same components as included in the prior art apparatus shown in FIG. 4.

In the air-fuel ratio control apparatus according to the invention, an oxygen sensor identical with the conventional one, e.g., the oxygen sensor 1C shown in FIG. 1, is disposed in an exhaust passage 32 so as to be situated on the upper-course side of a three-way catalyst 33. A carrier containing the oxygen storage component (OSC), e.g., the OSC-carrier monolith 38, is disposed in the passage 32 so as to be situated on the upper-course side of the sensor 1C.

The three-way catalyst 33 may be a conventional one using Pt, Rh, etc. The configuration of the catalyst 33 may be selected, as required, among various types including the monolith type, such as a honeycomb configuration, and the particle type, such as pellets, hollow cylinders, spheres, etc.

The OSC-carrier monolith 38 is not limited to a specific composition, and may be of any composition provided that it can carry the oxygen storage component. For example, the monolith 38 can be formed by combining the oxygen storage component with a monolith material which is obtained by applying a wash coat, composed mainly of alumina, to cordierite, for example. As mentioned before, cerium oxide ($CeO_2$), nickel oxide (NiO), copper oxide (CuO), etc., may be used as the oxygen storage component. Among these materials, cerium oxide is best suited for the purpose. If cerium oxide is used, the suitable amount of Ce ranges from 10 to 80 g/l, preferably 20 to 60 g/l.

The carrier to carry the oxygen storage component is not limited to the monolith type. Like the three-way catalyst 33 mentioned before, a particle type carrier, in the form of pellets, hollow cylinders, or spheres, may be used in place of the OSC-carrier monolith 38.

According to the air-fuel ratio control apparatus described above, the exhaust gas from the internal combustion engine 31 first passes through the OSC-carrier monolith 38, and is then introduced into the three-way catalyst 33. The oxygen sensor 1C detects the concentration of oxygen in the exhaust gas after the passage through the monolith 38, and delivers its detection signal to an electronic control unit 36. Thus, the OSC-carrier monolith 38 functions substantially in the same manner as the protective layer, the buffer layer, or the pellets of the oxygen sensor, carrying the oxygen storage component.

EXAMPLE 1

Figure 18:
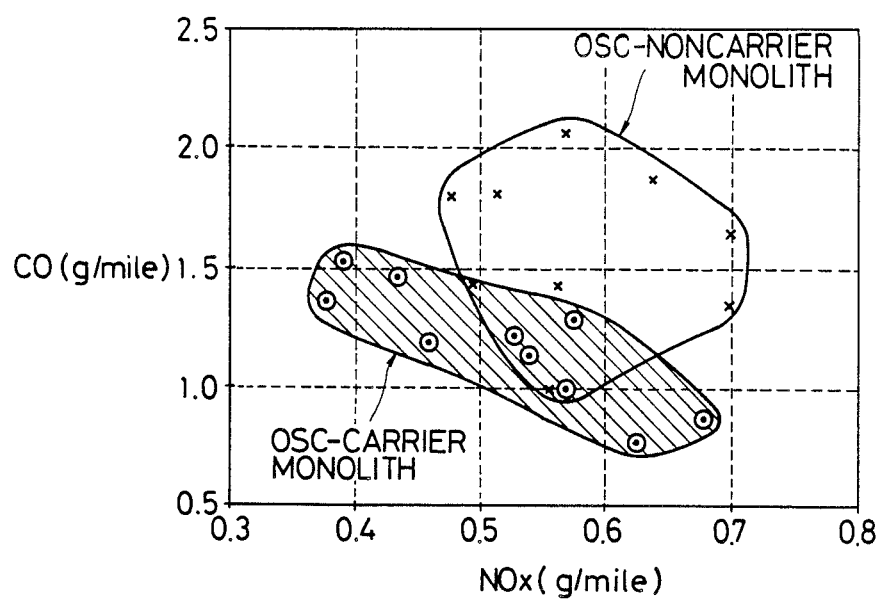
FIG. 18 is a graph showing the relationships between the respective amounts of discharge of $NO_x$ and CO as a result of evaluation tests for the exhaust gas characteristic of the air-fuel ratio control apparatus shown in FIG. 17.
Figure 19:
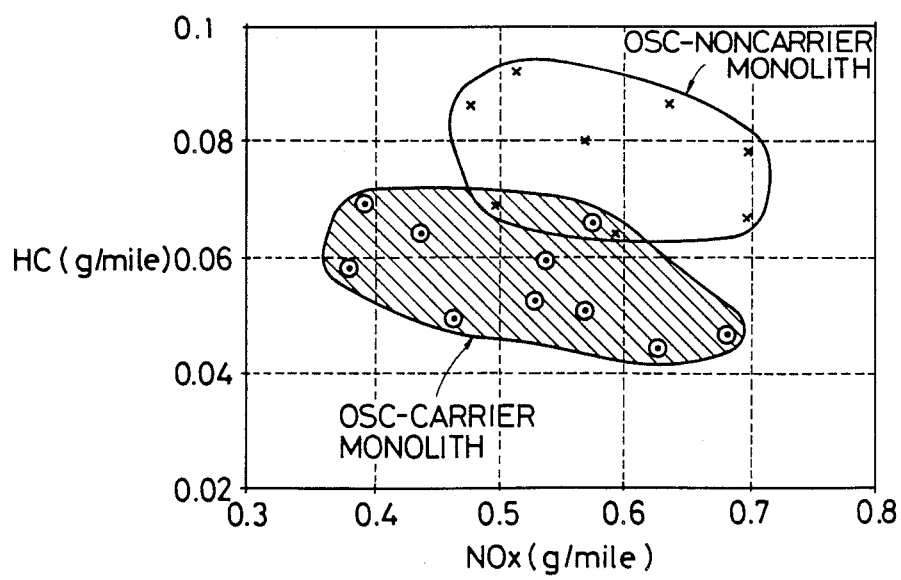
FIG. 19 is a graph, similar to FIG. 18, showing the relationships between the respective amounts of discharge of $NO_x$ and HC as a result of the evaluation tests for the exhaust gas characteristic.

Evaluation tests for the exhaust gas characteristic were conducted using the oxygen sensor 1 shown in FIG. 6 in place of the oxygen sensor 1C of the air-fuel ratio control apparatus shown in FIG. 4. In these tests, the type and amount of the oxygen storage component carried by the pellets 8 were varied. The arrangement of all the components of the ratio control apparatus except the oxygen sensor was unchanged. The constituents of the exhaust gas released into the atmosphere by way of the three-way catalyst 33 were measured for each test. The results of the measurement are shown in Table 1. The engine 31 was operated in the same manner for all the sample oxygen sensors. The engine 31 used was an engine of the so-called multi-point injection type in which a fuel injection valve 35 is provided for each cylinder. This engine was driven in the Los Angeles test mode LA-4, and the respective amounts of CO, HC, and $NO_X$ for second-peak acceleration (from 30 km/h to 74 km/h), as provided by the LA-4 mode, were obtained. A pair of oxygen sensors were provided for each type, and the average of discharge rates obtained from the tests on the two sensors was calculated and used as a test result. In Table 1, the respective discharge rates of the individual ingredients are given as comparative values (discharge indexes) based on the discharge rates (reference value 100) of the ingredients obtained with use of the prior art oxygen sensor 1C shown in FIG. 1, which does not use the pellets carrying the oxygen storage component. In general, the engine has an exhaust gas characteristic such that CO and unburned hydrocarbon (HC) have a discharge tendency opposite to that of $NO_X$; the discharge rate of the former decreases as that of the latter increases. For convenience of comparison of performance between the oxygen sensors, therefore, Table 1 shows the product ($CO*NO_X$) of the comparative values of discharge rate of CO and $NO_X$ and the product ($HC*NO_X$) of the comparative values of discharge rate of HC and $NO_X$.

in place of the monolith 38. The results of these tests are shown in FIGS. 18 and 19. In these tests, two sets of oxygen sensors, each including ten sensors different in responsiveness, were prepared, and the effect of improvement by the OSC-carrier monolith was examined for each set. The method, conditions, and other particulars of these tests are the same as the ones used in Example 1. In FIGS. 18 and 19, the plots within the hatched regions indicate the measurement results for the exhaust-gas ingredients obtained with use of the OSC-carrier monolith 38, while those within the plain regions indicate the results obtained with use of the OSC-noncarrier monolith. If the oxygen sensors vary in responsiveness, the exhaust gas characteristic of the engine 31 also varies. As seen from FIGS. 18 and 19, however, the exhaust gas characteristic is considerably improved by the used of the OSC-carrier monolith 38.

Figure 20:
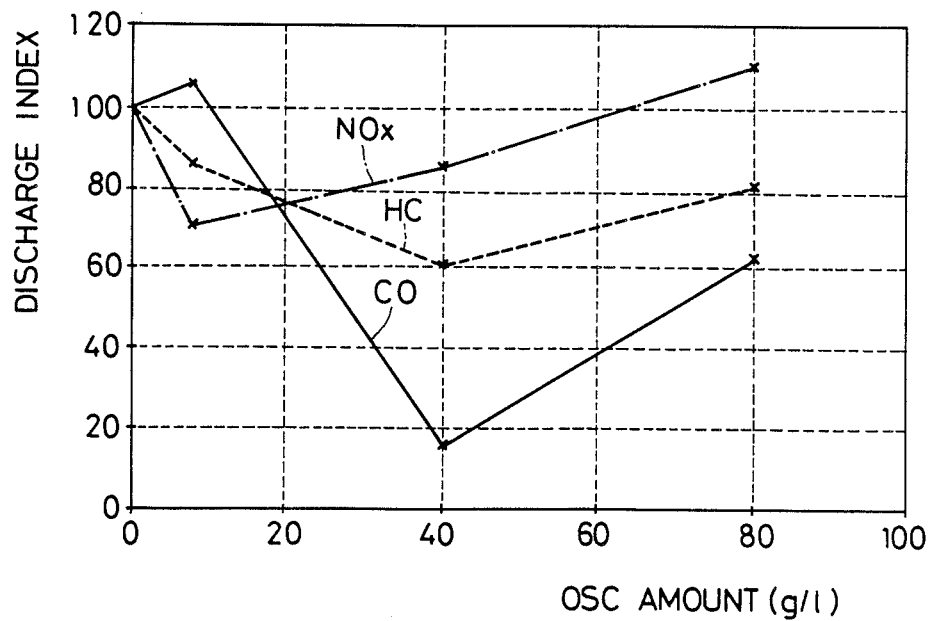
FIG. 20 is a graph showing the relationships between the respective discharge indexes of $NO_x$, CO, and HC and the amount of oxygen storage component carried by an OSC-carrier monolith of the air-fuel ratio control apparatus shown in FIG. 17.

FIG. 20 shows the results of tests on the air-fuel ratio control apparatus shown in FIG. 17, indicating the

TABLE 1

| TEST NO. | OXYGEN SENSOR | OSC | AMOUNT OF OSC CARRIED (g/l) | PELLET DIAMETER (mm) | CO | HC | $NO_x$ | $CO*NO_x$ | $HC*NO_x$ | EVALUATION |
|---|---|---|---|---|---|---|---|---|---|---|
| 1 | CONTROL | — | — | — | 100 | 100 | 100 | 100 | 100 | — |
| 2 | CONTROL | — | 0 | 4 | 91 | 100 | 102 | 92 | 102 | x |
| 3 | INVENTION | — | 0 | 2 | 102 | 109 | 73 | 77 | 80 | Δ |
| 4 | INVENTION | $CeO_2$ | 4 | 4 | 87 | 109 | 95 | 83 | 104 | Δ |
| 5 | INVENTION | $CeO_2$ | 8 | 4 | 46 | 83 | 85 | 42 | 71 | |
| 6 | INVENTION | $CeO_2$ | 16 | 4 | 53 | 92 | 119 | 64 | 110 | |
| 7 | INVENTION | $CeO_2$ | 40 | 4 | 94 | 90 | 81 | 77 | 73 | |
| 8 | INVENTION | $CeO_2$ | 80 | 4 | 67 | 87 | 122 | 83 | 106 | Δ |
| 9 | INVENTION | $La_2O_3$ | 8 | 4 | 53 | 94 | 115 | 62 | 109 | Δ |
| 10 | INVENTION | $La_2O_3$ | 40 | 4 | 65 | 87 | 97 | 64 | 85 | |
| 11 | INVENTION | CuO | 8 | 4 | 66 | 93 | 131 | 86 | 122 | Δ |

TABLE 2

| TEST NO. | OXYGEN SENSOR | AMOUNT OF $CeO_2$ CARRIED BY PROTECTIVE LAYER (BUFFER LAYER) (% By weight) | CO | HC | $NO_x$ | $CO*NO_x$ | $HC*NO_x$ | EVALUATION |
|---|---|---|---|---|---|---|---|---|
| 1 | CONTROL | | 100 | 100 | 100 | 100 | 100 | — |
| 12 | INVENTION | 0.8 | 71 | 77 | 127 | 90 | 98 | Δ |
| 13 | INVENTION | 1.8 | 85 | 87 | 98 | 83 | 85 | |
| 14 | INVENTION | 3.2 | 73 | 85 | 92 | 67 | 78 | |
| 15 | INVENTION | 8.0 | 79 | 94 | 99 | 78 | 93 | |
| 16 | INVENTION | 18.0 | 70 | 74 | 140 | 98 | 104 | Δ |

Actually, the given figures represent indexes or the quotients of the obtained products divided by 100. As for the evaluation marks, a double circle indicates a remarkable improvement effect; a circle, a moderate improvement effect; a triangular, a minimal effect of improvement compared with the conventional oxygen sensors; and a cross, no improvement effect.

EXAMPLE 2

Evaluation tests for the exhaust gas characteristic were conducted in the same manner as in Example 1, using the oxygen sensors of the type shown in FIG. 8. Table 2 shows the results of these tests. The method, conditions, and the way of evaluation of these tests are the same as the ones used in Example 1, and their description is omitted herein.

EXAMPLE 3

Exhaust-gas characteristic evaluation tests were conducted on the air-fuel ratio control apparatus with the OSC-carrier monolith 38 shown in FIG. 17 and the prior art air-fuel ratio control apparatus in which an OSC-noncarrier monolith having the same shape is used discharge rates for CO, HC, and $NO_X$ for the second-peak acceleration (from 30 km/h to 74 km/h), as provided by the LA-4 mode, obtained by varying the amount of the OSC carried by the OSC-carrier monolith 38. The resulting figures are given by discharge indexes calculated on the assumption that each discharge rate obtained with use of the OSC-noncarrier monolith is 100. An effect of improvement of the exhaust gas characteristic can be noticed when the amount of the OSC carried by the OSC-carrier monolith 38 is within a set range of about 10 to 80 g/l. The discharge rates for CO, HC, and $NO_X$ for acceleration can all be reduced by setting the OSC amount within a range of 20 to 60 g/l. As shown in FIGS. 18 and 19, these discharge rates vary as the oxygen sensors used vary in responsiveness. Despite the difference in responsiveness between the oxygen sensors, however, substantially the same results can be obtained for the individual sensors if the discharge indexes are used to rearrange the data.

What is claimed is:

1. An oxygen sensor having a detecting element for detecting the concentration of oxygen contained in a subject gas, comprising:
a carrier carrying a substance adapted to adsorb or desorb the oxygen in said subject gas in accordance with the partial pressure of the oxygen,
whereby said subject gas reaches said detecting element through said carrier.

2. An oxygen sensor having a protector pipe, formed with a number of holes and adapted to be inserted into a subject gas, and a detecting element for detecting the concentration of oxygen contained in said subject gas, said detecting element being disposed in said protector pipe, comprising:
a plurality of pellets filling a gap between the inner wall of said protector pipe and said detecting element and carrying a substance adapted to adsorb or desorb the oxygen in said subject gas in accordance with the partial pressure of the oxygen, each said pellet having a diameter larger than that of each said hole,
whereby said subject gas reaches said detecting element through said pellets.

3. The oxygen sensor according to claim 2, wherein said substance to adsorb or desorb the oxygen essentially consists of cerium oxide.

4. The oxygen sensor according to claim 2, wherein said substance to adsorb or desorb the oxygen essentially consists of lanthanum oxide.

5. The oxygen sensor according to claim 2, wherein the amount of said substance to adsorb or desorb the oxygen contained in said pellets ranges from 4 to 80 g/l as calculated in terms of a metal constituting said substance.

6. The oxygen sensor according to claim 5, wherein said amount of content preferably ranges from 8 to 40 g/l.

7. The oxygen sensor according to claim 2, wherein said detecting element includes an oxygen ion conducting solid electrolyte layer and a pair of electrodes holding said solid electrolyte layer therebetween.

8. The oxygen sensor according to claim 2, wherein said detecting element includes an insulating supporter, a chip disposed on one side face of said supporter, and a pair of electrodes spaced at a predetermined distance from each other and connected to said chip, said chip being formed of a material adapted to change the electric resistance thereof in accordance with the concentration of oxygen in contact therewith.

9. The oxygen sensor according to claim 8, wherein said material whose electric resistance changes in accordance with the oxygen concentration essentially consists of titanium oxide.

10. An oxygen sensor adapted to detect the concentration of oxygen contained in a subject gas, and having an oxygen ion conducting solid electrolyte layer, a pair of electrodes holding said solid electrolyte layer therebetween, and a protective layer formed on the outer surface of the subject-side electrode, out of said pair of electrodes, comprising:
a substance contained in said protective layer and adapted to adsorb or desorb the oxygen in said subject gas in accordance with the partial pressure of the oxygen,
whereby said subject gas reaches said subject-side electrode through said protective layer.

11. The oxygen sensor according to claim 10, wherein said substance to adsorb or desorb the oxygen essentially consists of cerium oxide.

12. The oxygen sensor according to claim 10, wherein said substance to adsorb or desorb the oxygen essentially consists of lanthanum oxide.

13. The oxygen sensor according to claim 10, wherein the ratio of said substance to adsorb or desorb the oxygen contained in said protective layer ranges from 0.8 to 16% by weight as calculated in terms of a metal constituting said substance.

14. The oxygen sensor according to claim 13, wherein said ratio of content preferably ranges from 1.6 to 8% by weight.

15. An oxygen sensor adapted to detect the concentration of oxygen contained in a subject gas, and having an oxygen ion conducting solid electrolyte layer and a pair of electrodes holding said solid electrolyte layer therebetween, comprising:
a buffer layer formed on the outer surface of the subject-side electrode, out of said pair of electrodes, and containing a substance adapted to adsorb or desorb the oxygen in said subject gas in accordance with the partial pressure of the oxygen,
whereby said subject gas reaches said subject-side electrode through said buffer layer.

16. The oxygen sensor according to claim 15, wherein said substance to adsorb or desorb the oxygen essentially consists of cerium oxide.

17. The oxygen sensor according to claim 15, wherein said substance to adsorb or desorb the oxygen essentially consists of lanthanum oxide.

18. The oxygen sensor according to claim 15, wherein the ratio of said substance to adsorb or desorb the oxygen contained in said buffer layer ranges from 0.8 to 16% by weight as calculated in terms of a metal constituting said substance.

19. The oxygen sensor according to claim 15, further comprising a protective layer interposed between said subject-side electrode and said buffer layer.

20. An oxygen sensor adapted to detect the concentration of oxygen contained in a subject gas, and having an insulating supporter, a chip disposed on one side face of said supporter, and a pair of electrodes spaced at a predetermined distance from each other and connected to said chip, said chip being formed of a material adapted to change the electric resistance thereof in accordance with the concentration of oxygen in contact therewith, comprising:
a porous layer covering the subject-side surface of said chip and containing a substance adapted to adsorb or desorb the oxygen in said subject gas in accordance with the partial pressure of the oxygen,
whereby said subject gas reaches said chip through said porous layer.

21. The oxygen sensor according to claim 20, wherein said material whose electric resistance changes in accordance with the oxygen concentration essentially consists of titanium oxide.

22. The oxygen sensor according to claim 20, wherein said substance to adsorb or desorb the oxygen essentially consists of cerium oxide.

23. The oxygen sensor according to claim 20, wherein said substance to adsorb or desorb the oxygen essentially consists of lanthanum oxide.

24. The oxygen sensor according to claim 20, wherein the ratio of said substance to adsorb or desorb the oxygen contained in said buffer layer ranges from 0.8 to 16% by weight as calculated in terms of a metal constituting said substance.

25. The oxygen sensor according to claim 20, wherein said supporter has a recess formed in one side face thereof, and both said chip and said porous layer are disposed in said recess.

26. The oxygen sensor according to claim 1, wherein said oxygen sensor is applied to an air-fuel ratio control apparatus of an internal combustion engine, and is disposed in an exhaust passage of said internal combustion engine, said oxygen sensor being adapted to detect the concentration of oxygen in exhaust gas and deliver a detection signal, said air-fuel ratio control apparatus including fuel supply means for supplying fuel to said engine, whereby a control signal used to vary the amount of fuel supply to said engine is delivered to said fuel supply means in accordance with said detection signal from said oxygen sensor.

27. A air-fuel ratio control apparatus having an oxygen sensor, disposed in an exhaust passage of an internal combustion engine and adapted to detect the concentration of oxygen in exhaust gas and deliver a detection signal, and fuel supply means for supplying fuel to said engine, whereby a control signal used to vary the amount of fuel supply to said engine is delivered to said fuel supply means in accordance with said detection signal from said oxygen sensor, comprising:
 a carrier disposed in said exhaust passage on the upper-course side of said oxygen sensor, with respect to the flowing direction of said exhaust gas, and carrying a substance adapted to adsorb or desorb the oxygen in said exahust gas in accordance with the partial pressure of the oxygen,
 whereby said exhaust gas to be detected by means of said oxygen sensor reaches said oxygen sensor through said carrier.

* * * * *